United States Patent
He et al.

(10) Patent No.: US 8,912,309 B2
(45) Date of Patent: Dec. 16, 2014

(54) PREPARATION METHOD FOR CASPOFUNGIN

(75) Inventors: Bingming He, Shanghai (CN); Ming Li, Shanghai (CN); Zhijun Tang, Shanghai (CN); Xiaoming Ji, Shanghai (CN)

(73) Assignee: Shanghai Techwell Biopharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 13/884,686

(22) PCT Filed: Nov. 10, 2011

(86) PCT No.: PCT/CN2011/082020
§ 371 (c)(1),
(2), (4) Date: May 10, 2013

(87) PCT Pub. No.: WO2012/062212
PCT Pub. Date: May 18, 2012

(65) Prior Publication Data
US 2013/0231457 A1 Sep. 5, 2013

(30) Foreign Application Priority Data
Nov. 10, 2010 (CN) .......................... 2010 1 0538951

(51) Int. Cl.
*C07K 1/113* (2006.01)
*C07K 7/56* (2006.01)
*C07K 7/64* (2006.01)

(52) U.S. Cl.
CPC .... *C07K 7/64* (2013.01); *C07K 7/56* (2013.01)
USPC .......................................... 530/317; 530/345

(58) Field of Classification Search
None
See application file for complete search history.

(56) References Cited

U.S. PATENT DOCUMENTS

| 5,552,521 A * | 9/1996 | Belyk et al. .................... 530/317 |
| 2004/0158034 A1 * | 8/2004 | Belyk et al. .................... 530/317 |
| 2010/0168415 A1 * | 7/2010 | Lee et al. ...................... 540/460 |

FOREIGN PATENT DOCUMENTS

CN 101648994 A 2/2010

OTHER PUBLICATIONS

Machine translation of CN 101648994 (A) (Feb. 17, 2010).*
International Search Report from Application PCT/CN2011/082020, dated Feb. 23, 2012, 3 pages.

* cited by examiner

*Primary Examiner* — Jeffrey E Russel
(74) *Attorney, Agent, or Firm* — Hamre, Schumann, Mueller & Larson, P.C.

(57) ABSTRACT

Disclosed is a preparation method for caspofungin, comprising the steps: (a) a compound as represented in Formula 2 and a strong leaving group 5 are mixed to obtain a compound as represented in Formula 3; (b) the compound as represented in Formula 3 and ethylenediamine are mixed to obtain a compound as represented in Formula 4; and, (c) the compound as represented in Formula 4 is mixed with a hydroxyl protection agent, and then a borane complex is mixed in to obtain a compound as represented in Formula 1.

16 Claims, No Drawings

PREPARATION METHOD FOR CASPOFUNGIN

TECHNICAL FIELD

The present invention relates to the field of organic chemistry, particularly to the preparation method for caspofungin.

BACKGROUND

In 1974, it was discovered that echinocandin compounds possess excellent antibacterial activity. Thereafter, many semisynthetic echinocandin compounds have been studied for their pharmacologic activities. In 2001, caspofungin was approved by US FDA, which represents the landmark for the research of antifungal medicaments. Caspofungin, the chemical structure of which is shown by Formula 1, represents a broad-spectrum and low-toxic medicament with unique action site:

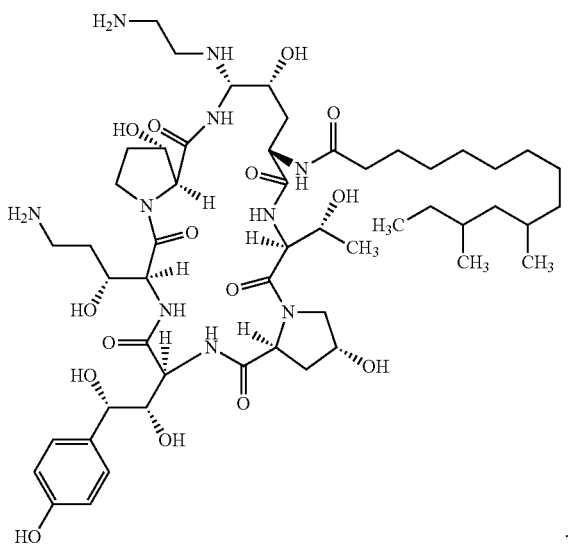

1

Caspofungin analogs and the preparation of Caspofungin have been described in WO94/21677, EP620232, WO96/24613, U.S. Pat. No. 5,552,521, WO97/47645, U.S. Pat. No. 5,936,062, WO02/083713, J. Org. Chem., 2007, 72, 2335-2343, CN101792486A, CN 101648994A, WO2010008493A2, US2010168415A1, EP1785432, and WO2010064219A1.

In WO94/21677 and EP 620232, the method for synthesizing and purifying caspofungin has been disclosed, comprising the following steps: Pneumocandin $B_0$ as the starting material reacts with alkyl thiol or aryl thiol, the resulting product is oxidized to obtain the sulfone intermediate, and then the sulfone intermediate reacts with amines in anhydrous non-proton solvent to obtain caspofungin, which was purified by chromatography.

According to WO96/24613 and U.S. Pat. No. 5,552,521, primary amide group in Pneumocandin $B_0$ is reduced to amine group (47% of yield), and then the resulting product reacts with thiophenol and ethylenediamine in turn to obtain caspofungin.

In WO97/47645, U.S. Pat. No. 5,936,062 and J. Org. Chem., 2007, 72, 2335-2343, two stereoselective methods for preparing caspofungin from Pneumocandin $B_0$ have been reported. In the first method, benzyl borate is used as protective group, amide group in Pneumocandin $B_0$ is reduced to amine group, and then the resulting product reacts with thiophenol and ethylenediamine in turn to obtain caspofungin; in the second method, Pneumocandin $B_0$ as the starting material reacts with thiophenol, the resulting product is protected by benzyl borate, the amide group in Pneumocandin $B_0$ is reduced to amine group, and then the resulting product reacts with ethylenediamine to obtain caspofungin.

In CN101792486A and CN 101648994A, a method has been disclosed, comprising the following steps: Pneumocandin $B_0$ as the starting material reacts with ethylenediamine under the protection of phenyl borate, and then the amide group in the resulting intermediate is reduced to amine group to obtain caspofungin.

In WO02/083713, US2010168415A1, EP1785432, WO2010064219A1, a method has been disclosed, comprising the following steps: the intermediate of Pneumocandin $B_0$ containing cyano is prepared, and then the intermediate is reduced by using hydrogen to obtain caspofungin.

According to WO2010008493A2, Pneumocandin $B_0$ as the starting material reacts with 4-methoxy thiophenol, the resulting product is protected by phenyl borate, the amide group in Pneumocandin $B_0$ is reduced to amine group under the condition of dehydration by 3A molecular sieve, and then the resulting product reacts with ethylenediamine to obtain caspofungin.

However, for the yield, purity, stability and waste, none of the disclosed methods is the optimal method for industrialization. The cost for industrialization will be greatly increased due to the repeated use of chromatographic column, thus resulting in great amount of waste. Some methods must be conducted under strict anhydrous conditions (such as, dehydration by 3A molecular sieve). Most of the methods use thiophenol with odor and high toxicity, are difficult to be operated, harmful to the operator and severely pollute the environment. Additionally, isomers are inevitably produced during the preparation of Pneumocandin $B_o$ containing cyano, the stereoselectivity and yield are not high, and expensive metals are used as catalysts, thereby resulting in high cost for industrialization. Therefore, it is urgent to develop a method for preparing caspofungin which is suitable for industrialization.

SUMMARY OF THE INVENTION

The subject of the present invention is to provide a novel method for preparing caspofungin.

In the present invention, a preparation method for the compound of Formula 1 is provided, said method comprising the following steps:

(a) mixing the compound of Formula 2 with strong leaving-group compound 5, thereby obtaining the compound of Formula 3;

(b) mixing the compound of Formula 3 with ethylenediamine to obtain the compound of Formula 4; and (c) mixing the compound of Formula 4 with a hydroxyl protectant, and then with a borane complex to obtain the compound of Formula 1;

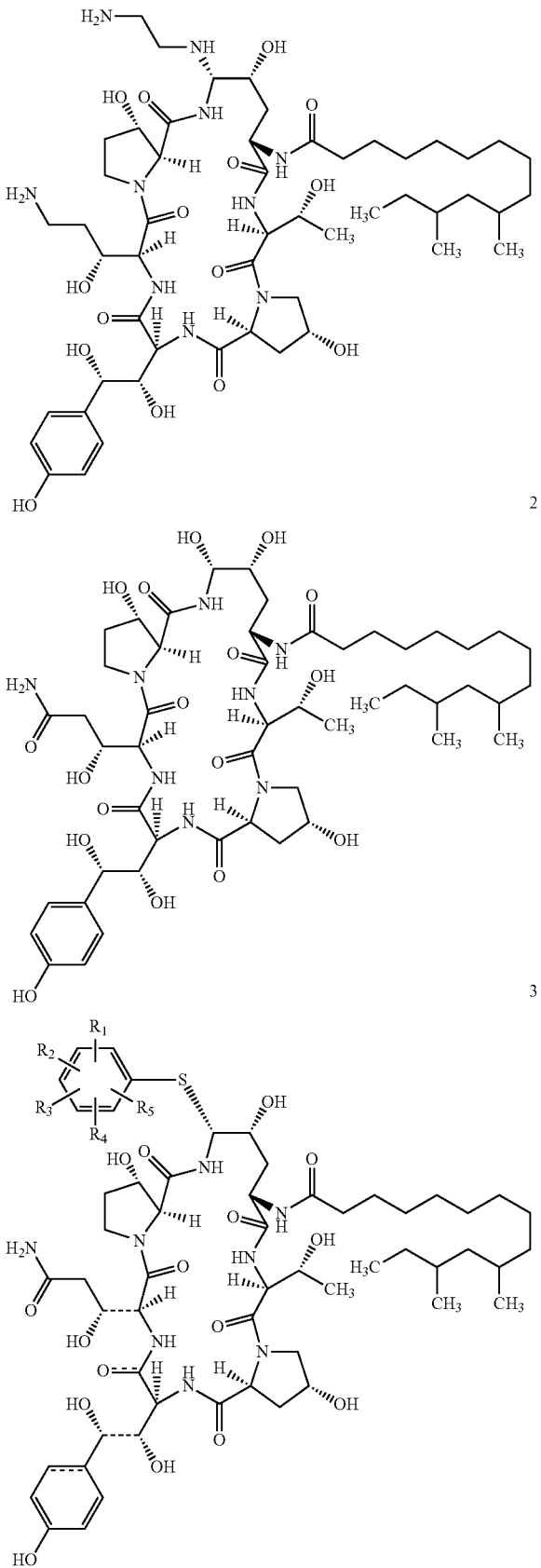

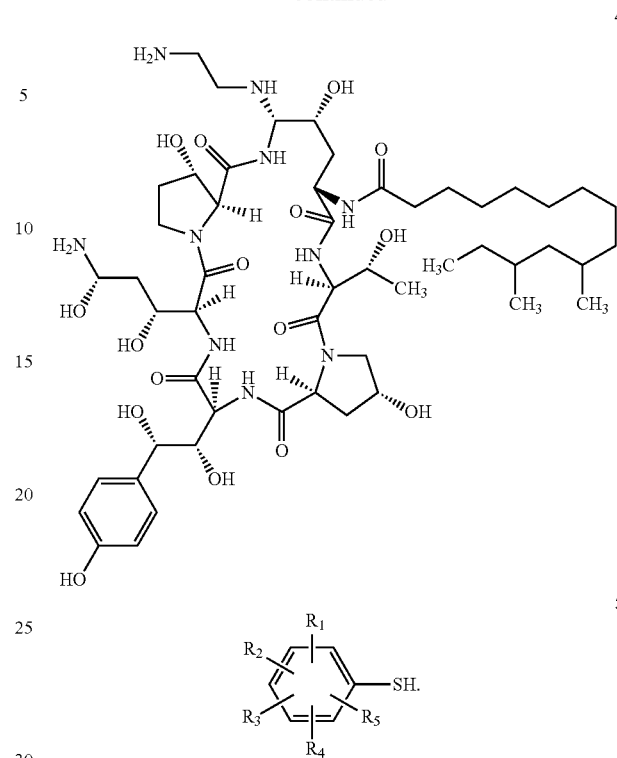

In step (a) of the above method, the strong leaving-group compound is sulphydryl-substituted aromatic ring compound 5, wherein $R_1$ is selected from hydroxy, benzyloxy, phenoxy, or substituted phenoxy, or substituted benzyloxy; $R_2$, $R_3$, $R_4$, $R_5$ is selected from hydrogen, C1-C6 alkyl, C1-C6 alkoxy, hydroxyl, or benzyloxyphenyl, substituted benzyloxyphenyl, nitro, fluorine, chlorine, bromine, iodine, respectively.

In the sulphydryl-substituted aromatic ring compound 5, $R_1$ is selected from hydroxy, benzyloxy, phenoxy, or substituted phenoxy; $R_2$, $R_3$, $R_4$, $R_5$ is selected from hydrogen, C1-C4 alkyl, C1-C4 alkoxy, hydroxyl, bromine or nitro.

Preferably, in the sulphydryl-substituted aromatic ring compound 5, $R_1$ is selected from hydroxy; $R_2$, $R_3$, $R_4$, $R_5$ is selected from hydrogen, methyl, or hydroxyl.

More preferably, compound 5 is selected from 4-hydroxy thiophenol, 3-hydroxy thiophenol, or 4-hydroxy-3-methyl thiophenol.

Most preferably, the sulphydryl-substituted aromatic ring compound 5 is selected from 4-hydroxy thiophenol.

In step (a) of the above method, the compound of Formula 2 is mixed with a strong leaving-group compound dissolved in an acid, wherein said acid is selected from trifluoroacetic acid, triflic acid, camphor sulfonic acid, methanesulfonic acid or p-toluene sulphonic acid.

In step (a) of the above method, the temperature for mixing is −50° C. to 40° C.; preferably, −20° C. to −15° C.

In step (b) of the above method, the compound of Formula 3 is mixed with ethylenediamine dissolved in the solvent selected from the following group: methanol, ethanol, tetrahydrofuran, 2-methyl tetrahydrofuran, isopropanol, trifluoroethanol, acetonitrile or dichloromethane.

In step (b) of the above method, the temperature for mixing is 0° C. to 40° C.; preferably, 25° C. to 35° C.

In step (c) of the above method, the hydroxyl protectant is selected from boric acid protectants or silicane agents.

In step (c) of the above method, the borane complex is selected from: the complex of borane and tetrahydrofuran, borane and dimethyl sulfide, borane and diphenyl sulfide, borane and dibenzyl sulfide, borane and dioxane, borane and 1,4-oxathiane, or the complex of $BH_2Cl$ and dimethyl sulfide; preferably, the complex of borane and tetrahydrofuran, or borane and dimethyl sulfide.

In step (c) of the above method, the temperature for mixing is −20° C. to 20° C.; preferably, 0° C. to 10° C.

Based on the above, a method for preparing caspofungin suitable for industrialization is provided in the present invention.

DETAILED DESCRIPTION OF THE INVENTION

The inventors have discovered a simple method for preparing the compound of Formula 1. Through a great deal of experiments, the inventors have discovered that the compound of Formula 3 can be obtained from the compound of Formula 2 through one-step operation, and the compound of Formula 1, i.e., caspofungin, can be obtained from the compound of Formula 3 through aminolysis using ethylenediamine and reduction reaction.

As used herein, chemical formulae or names should include all of the optical isomers and stereoisomers, as well as the mixture or racemic mixture comprising the isomers.

In the present invention, a preparation method for the compound of formula 1 is provided, said method comprising the following steps:

in the first step, the compound of Formula 2 is mixed with a strong leaving-group compound to obtain the compound of Formula 3;

the compound of Formula 3 is mixed with ethylenediamine to obtain the compound of Formula 4, and the compound of Formula 4 is mixed with a hydroxyl protectant and then with the borane complex to obtain the compound of Formula 1.

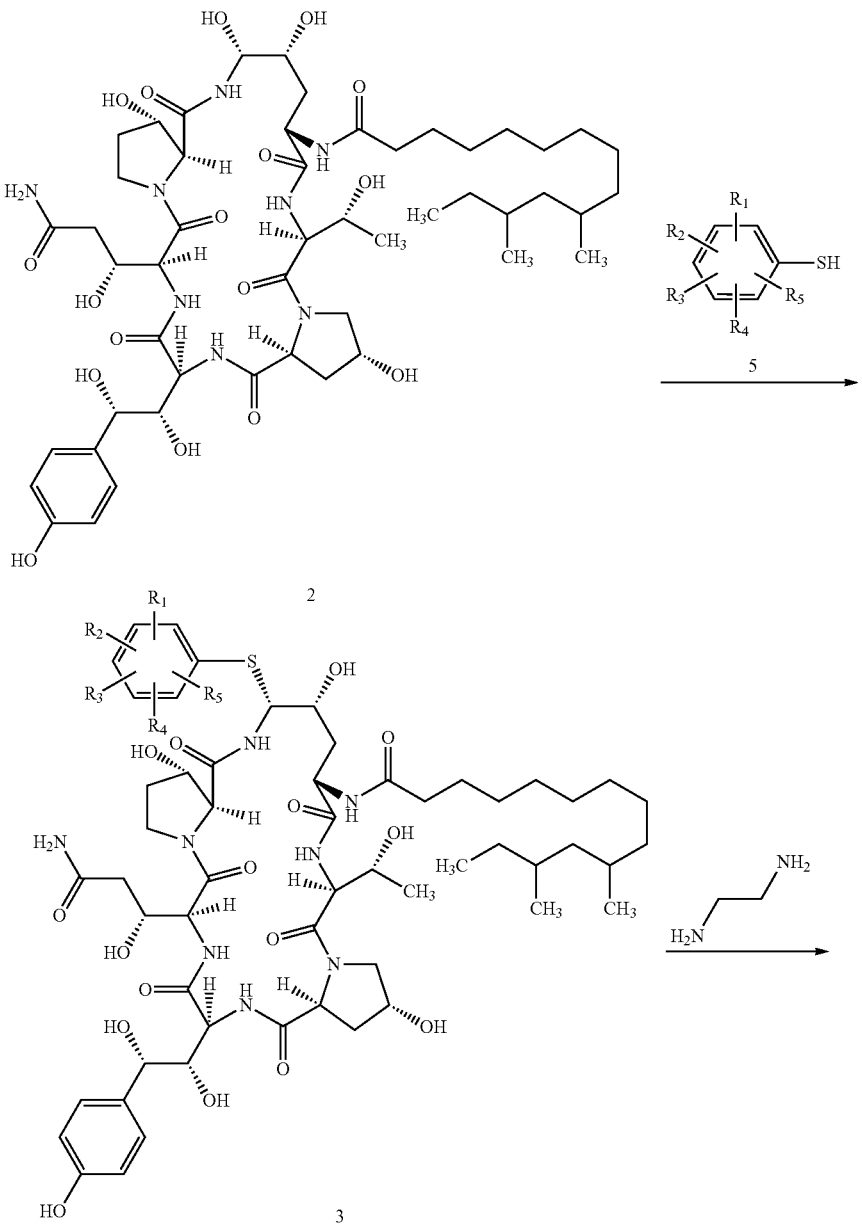

-continued

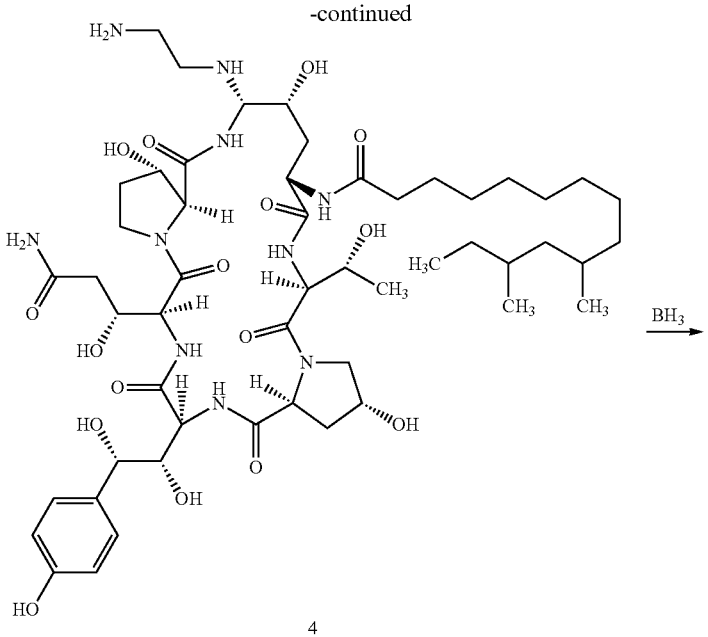

4

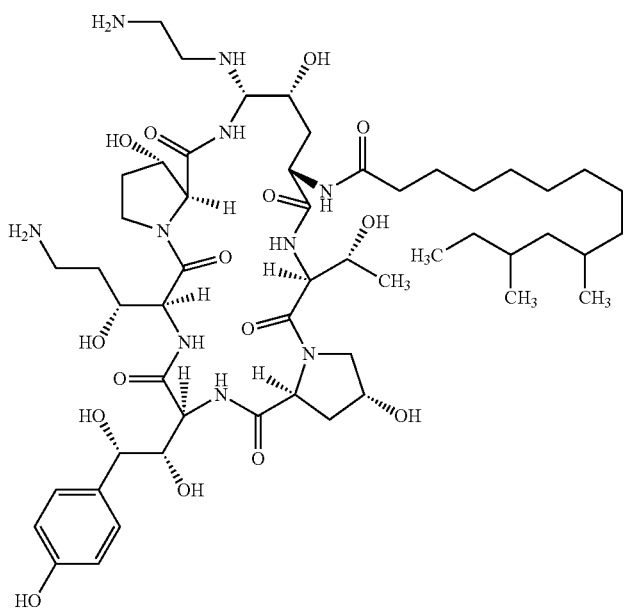

1

In the preparation method provided by the present invention, the starting material, i.e., the compound of Formula 2, can be obtained by the methods well-known in the art, for example (but not limited to), U.S. Pat. No. 5,021,341 (published on Jun. 4, 1991), culturing Zalerion arboricola ATCC 20868 in a medium rich in mannitol as the major carbon source.

In the present invention, the strong leaving-group compound is sulphydryl-substituted aromatic ring compound 5, wherein $R_1$ is selected from hydroxy, benzyloxy, phenoxy, substituted phenoxy, or substituted benzyloxy; $R_2, R_3, R_4, R_5$ is selected from hydrogen, C1-C6 alkyl, C1-C6 alkoxy, hydroxyl, or benzyloxyphenyl, substituted benzyloxyphenyl, nitro, fluorine, chlorine, bromine, iodine, respectively. Preferably, $R_1$ is selected from hydroxy, benzyloxy, phenoxy, or substituted phenoxy; $R_2, R_3, R_4, R_5$ is selected from hydrogen, C1-C4 alkyl, C1-C4 alkoxy, hydroxyl, bromine or nitro. More preferably, $R_1$ is selected from hydroxy; $R_3, R_4, R_5$ is selected from hydrogen, methyl, or hydroxyl. Most preferably, aromatic ring compound 5 is selected from 4-hydroxy thiophenol.

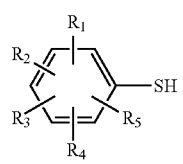

5

In the first step, the catalyst can be any acid with moderate intensity, for example (but not limited to) trifluoroacetic acid, triflic acid, camphor sulfonic acid, methanesulfonic acid or p-toluene sulphonic acid; preferably, triflic acid.

In one example of the present invention, the reaction of the first step can be conducted by reacting the compound of Formula 2 with 4-hydroxy thiophenol dissolved in acetonitrile and trifluoroacetic acid to produce the hydroxyl-substituted diphenyl sulfide intermediate, i.e., the compound of Formula 3. The reaction liquid is neutralized by aqueous sodium acetate and the stable intermediate in solid can be obtained.

According to one example of the present invention, in the reaction of the first step, phenyl boronic acid can be added to protect two adjacent hydroxyls in homotyrosine segment, thereby producing the phenyl borate intermediate 6 and significantly reducing the amount of the impurity, i.e., diphenyl sulfide compound 7. The temperature for reaction can also be reduced. Preferably, when phenyl boronic acid is used to protect the adjacent hydroxyls, a stronger acid, for example, triflic acid can be used as the catalyst.

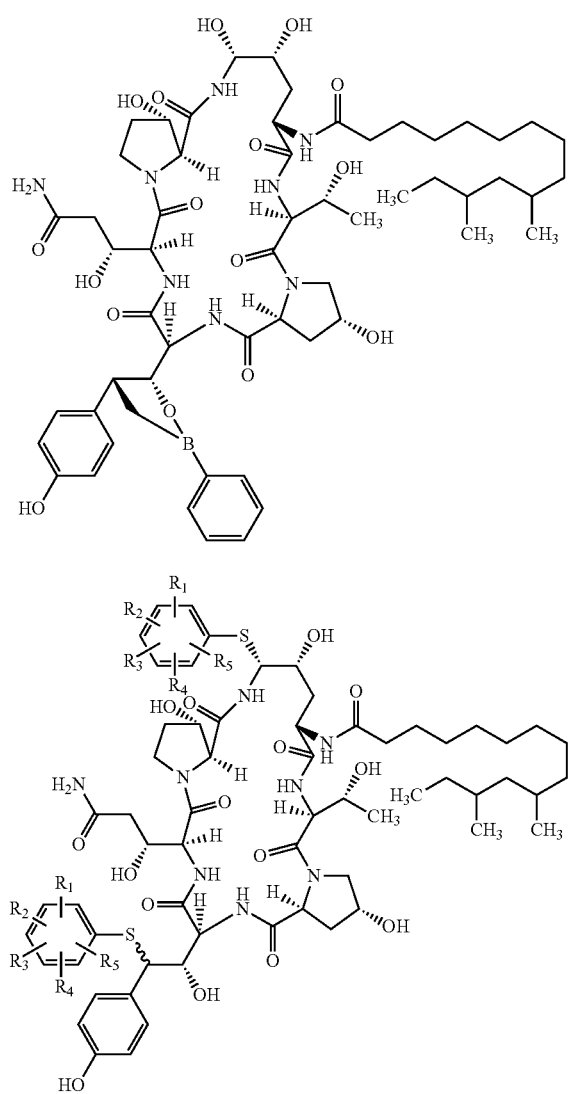

The amount of the final product depends on the amount of the compound 5 in this step. The highest production of the final product can be obtained at 3-5 equivalents.

In one preferred example of the present invention, 3-5 equivalent of 4-hydroxy thiophenol is used in the reaction of the first step. The preferable condition for forming sulfide is that 3 equivalents of 4-hydroxy thiophenol, 2 equivalents of phenyl boronic acid and 3 equivalents of triflic acid are dissolved in acetonitrile at −15° C., and the yield for the solid is 80-95%.

According to one example of the present invention, in the second step, the compound of Formula 3 reacts with ethylenediamine in a polar solvent to obtain the compound of Formula 4.

Preferably, the reaction can be conducted at the temperature of 0° C. to 40° C. for 0.5-96 hours. More preferably, the reaction can be conducted at the room temperature for 24-72 hours.

Preferably, the polar solvent is selected from methanol, ethanol, tetrahydrofuran, 2-methyl tetrahydrofuran, isopropanol, trifluoroethanol, acetonitrile or dichloromethane with methanol or ethanol being preferred.

In the examples of the present invention, after the second reaction is completed, acetic acid is used for regulating pH to 4-6, the reaction liquid is diluted by using water, and the dry intermediate in solid (i.e., the compound of Formula 4) is obtained by column chromatography, concentration or crystallization.

After the reaction is completed, acetic acid is used for regulating pH to 4-6, the reaction liquid is diluted by using water, and the dry intermediate in solid (i.e., the compound of Formula 4) is obtained by column chromatography, concentration or crystallization. In a preferred example of the present invention, the column chromatography is performed on reverse-phase column, and the aqueous organic solvent is used to elute the column. The organic solvent is selected from methanol, acetonitrile, ethanol, isopropanol and the like, with acetonitrile being preferred.

In the step for reducing the amide (the compound of Formula 4) into amine, the reductant is selected from borane complex, or metal boride, titanium or zirconium boride dissolved in THF or other suitable solvents, or the complex of borane and ammonia, dimethylamine, pyridine or piperazine. The preferred reductant is borane complex, which can be selected from the complex of borane and tetrahydrofuran, dimethyl sulfide, diphenyl sulfide, dibenzyl sulfide, dioxane, 1,4-oxathiane, or the complex of $BH_2Cl$ and dimethyl sulfide; preferably, the complex of borane and tetrahydrofuran, or borane and dimethyl sulfide. The metal boride dissolved in THF or other suitable solvents is selected from the complex of $ZrCl_4/NaBH_4$ or $TiCl_4/NaBH_4$. The raw material which is not reduced to amine by the reductant can be separated by reverse-phase chromatography.

In one preferred example of the present invention, the two adjacent hydroxyls in homotyrosine segment are protected in advance, N,O-bis(trimethylsilyl)trifluoroacetamide (BSTFA) is used to protect the remaining hydroxyls and amino to obtain homogeneous reaction liquid, thereby significantly increasing the yield for the reaction. The preferred conditions are listed as follows: at 10° C. to 68° C., the compound of Formula 4 reacts with 1.1-3.0 equiv of phenyl boric acid in tetrahydrofuran, 3-9 equiv of BSTFA is added at 0° C. to 68° C. to obtain homogeneous reaction liquid, borane is added at −30° C. to 30° C. to obtain the compound of formula 1, the reaction is quenched by hydrochloric acid, and then the purified compound of Formula 1 is obtained by column chromatography and crystallization.

All the features mentioned above or in the examples below of the invention can be optionally combined. All features disclosed in this specification may be used in any combination. Any alternative feature serving the same, equivalent, or similar purpose may replace each feature disclosed in this specification. Therefore, unless otherwise specified, the features as disclosed are only general examples of equivalent or similar features.

The main advantages of the invention include:
1. A new method for preparing caspofungin is provided.
2. The method has many advantages, such as short synthesis route, mild reaction condition, simple post-treatment and increased yield. Additionally, thiophenol with odor and high toxicity is not used, thereby not polluting the environment or harming the operators, and the difficulty for operation and the requirement to the equipments are reduced, thereby significantly reducing the cost.
3. In the new preparation method for caspofungin provided by the invention, the compound of Formula 2 obtained by fermentation is used as the starting material, and the intermediates produced in the synthesis steps are stable, therefore, the quality of the intermediate and final product can be controlled, thereby facilitating the industrialization.

The invention will be further illustrated with reference to the following specific examples. It is to be understood that these examples are only intended to illustrate the invention, but not to limit the scope of the invention. For the experimental methods in the following examples without particular conditions, they are performed under routine conditions or as instructed by the manufacturer. Unless otherwise specified, all percentages, ratios, proportions or parts are by weight.

The unit of the weight/volume percentages in the invention is well known to the skilled in the art, for example, the weight of a solute in a 100 mL solution.

Unless otherwise defined, all scientific and technical terms used herein have the same meaning as commonly understood by the skilled in the art. Furthermore, any process or material similar or equivalent to those described herein can be used in the process of the present invention. The preferred embodiments and materials described herein are merely provided for illustration.

Example 1

Preparation of the Compound of Formula 3a from the Compound of Formula 2

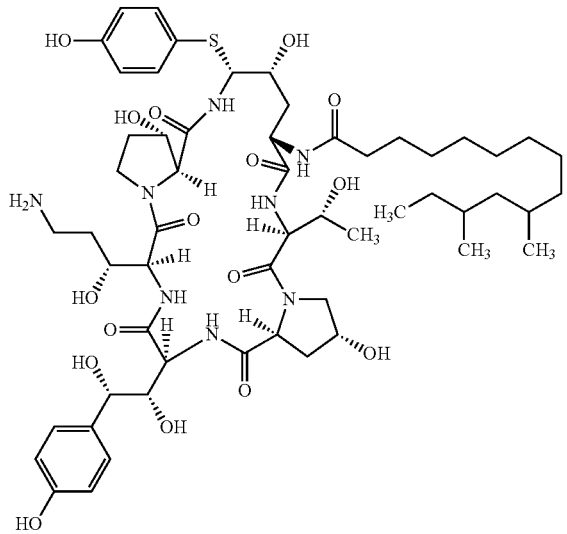

Under $N_2$, acetonitrile (150 ml), the compound of Formula 2 (5.0 g), phenyl boronic acid (0.60 g) and 4-hydroxy thiophenol (1.81 g) were mixed homogeneously. The reaction temperature was reduced to −20 to −15° C. Triflic acid (1.25 ml) was added dropwise. Upon addition, the reaction was conducted at −20 to −15° C. for about 2.5 h. The reaction was monitored by TLC. Upon completion, the reaction was quenched, and aqueous NaOAc (1.15 g NaOAc dissolved in 25 ml of water) was slowly added. Upon addition, the reaction temperature was increased to 20° C., and the solution was agitated for 2 h. Great amount of solid was precipitated, and the temperature was reduced to below 0° C. The reaction mixture was filtrated. The filter cake was washed with 60 ml of acetonitrile/water=9:1 (V/V) for 3 times and dried under vacuum for 5 h to obtain the compound of Formula 3a (4.76 g, yield 95.2%). (the yield was calculated based on the weight).

Example 2

Preparation of the Compound of Formula 4 from the Compound of Formula 3a

Under $N_2$, the compound of Formula 3a (2.0 g) was dissolved in methanol (8.5 ml), and the temperature of the solution was reduced to −20 to −15° C. Ethylenediamine (8.5 ml) was added dropwise. Upon addition, the temperature was increased to 30 to 35° C., and the reaction was conducted for 48 h. The conversion rate for the reaction was 99% monitored by HPLC. The reaction liquid was added into acetic acid (16.6 ml) in water (36.3 ml) dropwise, and the resulting solution was diluted with water for one time and loaded onto a preparative column. The column was eluted with 22% acetonitrile/water (0.15% acetic acid). The collections rich in the product were pooled, diluted with water for one time and loaded onto a preparative column. The column was eluted with 90% acetonitrile/water (0.15% acetic acid), and effluents were collected and concentrated to dryness under reduced pressure to obtain the compound of Formula 4 (1.90 g, the purity=95.0% by HPLC) in white solid. To the compound, methanol (8 ml) was added and the solution was agitated for dissolving the compound. Ethyl acetate (24 ml) was added dropwise at room temperature, the resulting solution was agitated for 2 h at room temperature. The solution was cooled and filtered, and the resulting solid was dried to obtain the compound of Formula 4 (1.84 g, yield 92%).

Example 3

Preparation of the Compound of Formula 1 from the Compound of Formula 4

Under $N_2$, the compound of Formula 4 (1.0 g), phenyl boronic acid (0.14 g), tetrahydrofuran (40 ml) were refluxed for 30 min. The reaction mixture was cooled to the room temperature, and BSTFA (1.06 ml) was added and the solution was agitated for 1 h at the room temperature. The reaction mixture was cooled to −10 to −5° C., and the complex of borane and dimethyl sulfide (0.4 ml, 0.94%) was added dropwise. Upon addition, the reaction mixture was warmed to 10 to 15° C., and the reaction was conducted for 3.5 h. The conversion rate for the reaction was 82% monitored by HPLC. Afterwards, 2 N hydrochloric acid (2.4 ml) was added dropwise, and water (80 ml) was added. Upon addition, the reaction mixture was agitated for 24 h at the room temperature. The reaction was diluted with water, and loaded onto a preparative column. The column was eluted with 22% acetonitrile/water (0.15% acetic acid). The collections rich in the product were pooled, diluted with water for one time and loaded onto a preparative column. The column was eluted with 90% acetonitrile/water (0.15% acetic acid), and effluents were collected and lyophilized to obtain the crude caspofungin diacetate (0.80 g, yield 80%, the purity=98.0% by HPLC) in white solid. The crude caspofungin was dissolved into ethanol (6 ml) and 6% aqueous acetic acid (0.6 ml), and then ethyl acetate (10.5 ml) was added dropwise. The whole system was agitated for 1 h at 10° C. and then filtered, and the obtained solid was dried to obtain caspofungin diacetate (the compound of Formula 1) (0.75 g, yield 75%).

MS(ESI): 1093.6 (M+H+);

$^1$H-NMR (500.13 MHz, CD3OD) δ 7.12 (m, 2H), 6.75 (m, 2H), 4.97 (d, 1H), 4.91 (d, 1H), 4.66 (d, 1H), 4.60 (dd, 3.2, 1H), 4.56-4.51 (m 2H), 4.48 (dd, 1H), 4.32-4.28 (m, 3H) 4.22 (dd, 1H), 4.18 (d, 1H), 4.08-3.96 (m, 3H), 3.83 (m, 1H), 3.76 (d, 1H), 3.05 (t, 2H), 3.02-2.76 (m, 4H), 2.41 (dd, 1H), 2.29-2.17 (m, 3H) 2.11-1.78 (m, 5H), 1.90 (s, 6H), 1.58 (m, 2H), 1.53-1.19 (m, 15H), 1.16 (d, 3H), 1.13-1.00 (m, 2H), 0.91 (m, 1H), 0.87 (t, 3H), 0.85 (degenerated, 6H);

$^{13}$C-NMR (125 MHz, CD3OD) 180.7, 176.7, 174.6, 171.1, 174.0, 173.3, 173.2, 169.4, 159.1, 116.7, 77.8, 76.1, 75.5, 72.5, 71.8, 70.6, 69.8, 64.8, 63.3, 58.9, 58.8, 57.6, 56.7, 56.5, 51.6, 47.5, 46.4, 44.5, 40.9, 39.5, 38.8, 38.5, 37.4, 36.2, 35.1, 33.4, 31.7, 31.6, 31.4 31.3, 31.1, 30.84, 30.81, 28.5, 27.5, 24.8.

Example 4

Preparation of the Compound of Formula 3b from the Compound of Formula 2

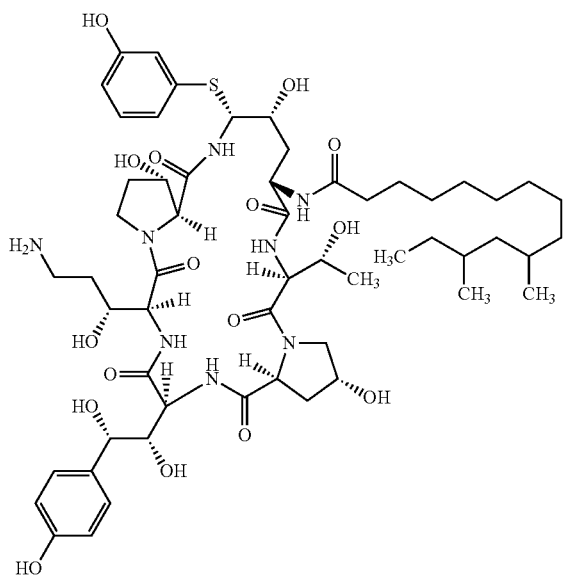

3b

Under N$_2$, acetonitrile (100 ml), the compound of Formula 2 (5.0 g), phenyl boronic acid (0.90 g) and 3-hydroxy thiophenol (1.80 g) were mixed homogeneously. The reaction temperature was reduced to below −50° C. Triflic acid (1.05 ml) was added dropwise. Upon addition, the reaction was conducted at −50 to −45° C. for about 2.5 h. The reaction was monitored by TLC. Upon completion, the reaction was quenched, and aqueous NaOAc (1.15 g NaOAc dissolved in 25 ml of water) was slowly added. Upon addition, the reaction temperature was increased to 20° C., and the reaction was agitated for 2 h. Great amount of solid was precipitated, and the temperature was reduced to below 0° C. The reaction mixture was filtrated. The filter cake was washed with 60 ml of acetonitrile/water=9:1 (V/V) for 3 times and dried under vacuum for 5 h to obtain the compound of Formula 3b (4.65 g, yield 93%).

Example 5

Preparation of the Compound of Formula 4 from the Compound of Formula 3b

Under N$_2$, the compound of Formula 4 (1.0 g), phenyl boronic acid (0.36 g), tetrahydrofuran (40 ml) were refluxed for 30 min. The reaction mixture was cooled to the room temperature, and BSTFA (2.0 ml) was added and the solution was agitated for 1 h at the room temperature. The temperature was maintained at −20 to −15° C., and the complex of borane and tetrahydrofuran in tetrahydrofuran (6.8 ml, 1 M) was added dropwise. Upon addition, the reaction was conducted at −20 to −15° C. for 3.5 h. The conversion rate for the reaction was 81% monitored by HPLC. Afterwards, 2 N hydrochloric acid (2.4 ml) was added dropwise, and water (80 ml) was added. Upon addition, the reaction mixture was agitated for 24 h at the room temperature. The reaction was diluted with water, and loaded onto a preparative column. The column was eluted with 22% acetonitrile/water (0.15% acetic acid). The collections rich in the product were pooled, diluted with water for one time and loaded onto a preparative column. The column was eluted with 90% acetonitrile/water (0.15% acetic acid), and effluents were collected and lyophilized to obtain the crude caspofungin diacetate (0.77 g, yield 77%, the purity=98.3% by HPLC) in white solid. The crude caspofungin was dissolved into ethanol (6 ml) and 6% aqueous acetic acid (0.6 ml), and then ethyl acetate (11 ml) was added dropwise. The whole system was agitated for 1 h at 10° C., and filtered, and the obtained solid was dried to obtain caspofungin diacetate (the compound of Formula 1) (0.72 g, yield 72%).

Example 6

Preparation of the Compound of Formula 1 from the Compound of Formula 4

Under N$_2$, the compound of Formula 4 (1.0 g), phenyl boronic acid (0.36 g), tetrahydrofuran (40 ml) were refluxed for 30 min. The reaction mixture was cooled to the room temperature, and BSTFA (2.0 ml) was added and the solution was agitated for 1 h at the room temperature. The temperature was maintained at −20 to −15° C., and the complex of borane and tetrahydrofuran in tetrahydrofuran (6.8 ml, 1 M) was added dropwise. Upon addition, the reaction was conducted at −20 to −15° C. for 3.5 h. The conversion rate for the reaction was 81% monitored by HPLC. Afterwards, 2 N hydrochloric acid (2.4 ml) was added dropwise, and water (80 ml) was added. Upon addition, the reaction mixture was agitated for 24 h at the room temperature. The reaction was diluted with water, and loaded onto a preparative column. The column was eluted with 22% acetonitrile/water (0.15% acetic acid). The collections rich in the product were pooled, diluted with water for one time and loaded onto a preparative column. The column was eluted with 90% acetonitrile/water (0.15% acetic acid), and effluents were collected and lyophilized to obtain the crude caspofungin diaectate (0.77 g, yield 77%, the purity=98.3% by HPLC) in white solid. The crude caspofungin was dissolved into ethanol (6 ml) and 6% aqueous acetic acid (0.6 ml), and then ethyl acetate (11 ml) was added dropwise. The whole system was agitated for 1 h at 10° C., and filtered, and the obtained solid was dried to obtain caspofungin diaectate (the compound of Formula 1) (0.72 g, yield 72%).

Example 7

Preparation of the Compound of Formula 3c from the Compound of Formula 2

3c

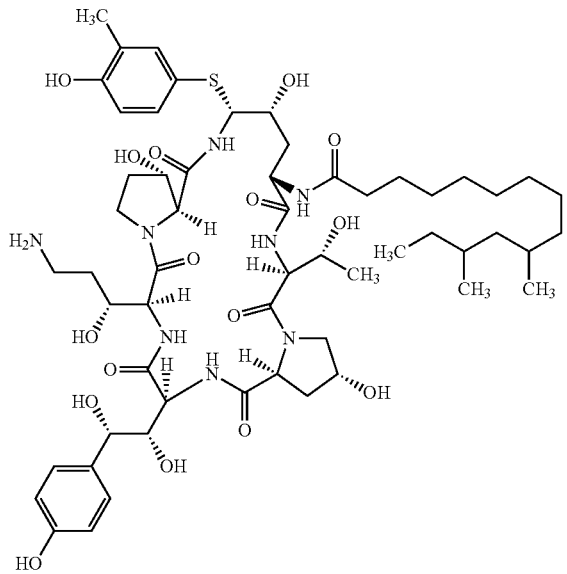

Under $N_2$, acetonitrile (200 ml), the compound of Formula 2 (5.0 g), phenyl boronic acid (1.50 g) and 4-hydroxy-3-methyl thiophenol (2.05 g) were mixed homogeneously. The reaction temperature was reduced to −50 to −45° C. Methanesulfonic acid (1.36 g) was slowly added. Upon addition, the temperature was reduced to −50 to −45° C., and the reaction was conducted for about 2.5 h. The reaction was monitored by TLC. Upon completion, the reaction was quenched, and aqueous NaOAc (1.20 g NaOAc dissolved in 20 ml of water) was slowly added. Upon addition, the reaction temperature was increased to 20° C., and the solution was agitated for 2 h. Great amount of solid was precipitated, and the temperature was reduced to below 0° C. The reaction mixture was filtrated. The filter cake was washed with 50 ml of acetonitrile/water=9:1 (V/V) for 3 times and dried under vacuum for 5 h to obtain the compound of Formula 3c (4.60 g, yield 92%).

Example 8

Preparation of the Compound of Formula 4 from the Compound of Formula 3c

Under $N_2$, the compound of Formula 3c (2.0 g) was dissolved in ethanol (10 ml). Ethylenediamine (10 ml) was added dropwise at 35 to 40° C. Upon addition, the reaction was conducted for 24 h at 35 to 40° C. The conversion rate for the reaction was 98% monitored by HPLC. The reaction liquid was added into acetic acid (16.6 ml) in water (36.3 ml) dropwise, and the resulting solution was diluted with water for one time and loaded onto a preparative column. The column was eluted with 22% acetonitrile/water (0.15% acetic acid). The collections rich in the product were pooled, diluted with water for one time and loaded onto a preparative column. The column was eluted with 90% acetonitrile/water (0.15% acetic acid), and effluents were collected and concentrated to dryness under reduced pressure to obtain the compound of Formula 4 (1.88 g, the purity=96.0% by HPLC) in white solid. To the compound, methanol (8 ml) was added and the solution was agitated for dissolving the compound. Ethyl acetate (24 ml) was added dropwise at room temperature, the resulting solution was agitated for 2 h at room temperature. The solution was cooled and filtered, and the resulting solid was dried to obtain the compound of Formula 4 (1.82 g, yield 91%).

Example 9

Preparation of the Compound of Formula 1 from the Compound of Formula 4

Under $N_2$, the compound of Formula 4 (1.0 g), phenyl boronic acid (0.24 g), tetrahydrofuran (40 ml) were refluxed for 30 min. The reaction mixture was cooled to the room temperature, and BSTFA (2.4 ml) was added and the solution was agitated for 1 h at the room temperature. The temperature was maintained at 15 to 20° C., and the complex of borane and dimethyl sulfide (0.8 ml, 0.94%) was added dropwise. Upon addition, the reaction was conducted at 15 to 20° C. for 3.5 h. The conversion rate for the reaction was 85% monitored by HPLC. Afterwards, 2 N hydrochloric acid (2.4 ml) was added dropwise, and water (100 ml) was added. Upon addition, the reaction mixture was agitated for 24 h at the room temperature. The reaction was diluted with water, and loaded onto a preparative column. The column was eluted with 22% acetonitrile/water (0.15% acetic acid). The collections rich in the product were pooled, diluted with water for one time and loaded onto a preparative column. The column was eluted with 90% acetonitrile/water (0.15% acetic acid), and effluents were collected and lyophilized to obtain the crude caspofungin diacetate (0.82 g, yield 82%, the purity=98.3% by HPLC) in white solid. The crude caspofungin was dissolved into ethanol (6 ml) and 6% aqueous acetic acid (0.6 ml), and then ethyl acetate (11 ml) was added dropwise. The whole system was agitated for 1 h at 10° C., and filtered, and the obtained solid was dried to obtain caspofungin diacetate (the compound of Formula 1) (0.79 g, yield 79%).

The above examples are merely the preferred examples for the present invention, and such examples cannot be used to limit the scope of the invention. The substantial technical contents according to the present invention are broadly defined in the claims. And any entities or methods accomplished by others should be considered as the equivalents and fall within the scope as defined by the claims, if said entities or methods are the same as those defined by the claims.

The invention claimed is:

1. A preparation method for the compound of Formula 1, wherein said method comprises the following steps:
    (a) mixing the compound of Formula 2 with a strong leaving-group compound 5, thereby obtaining the compound of Formula 3;
    (b) mixing the compound of Formula 3 with ethylenediamine to obtain the compound of Formula 4; and
    (c) mixing the compound of Formula 4 with a hydroxyl protectant, and then with a borane complex to obtain the compound of Formula 1;

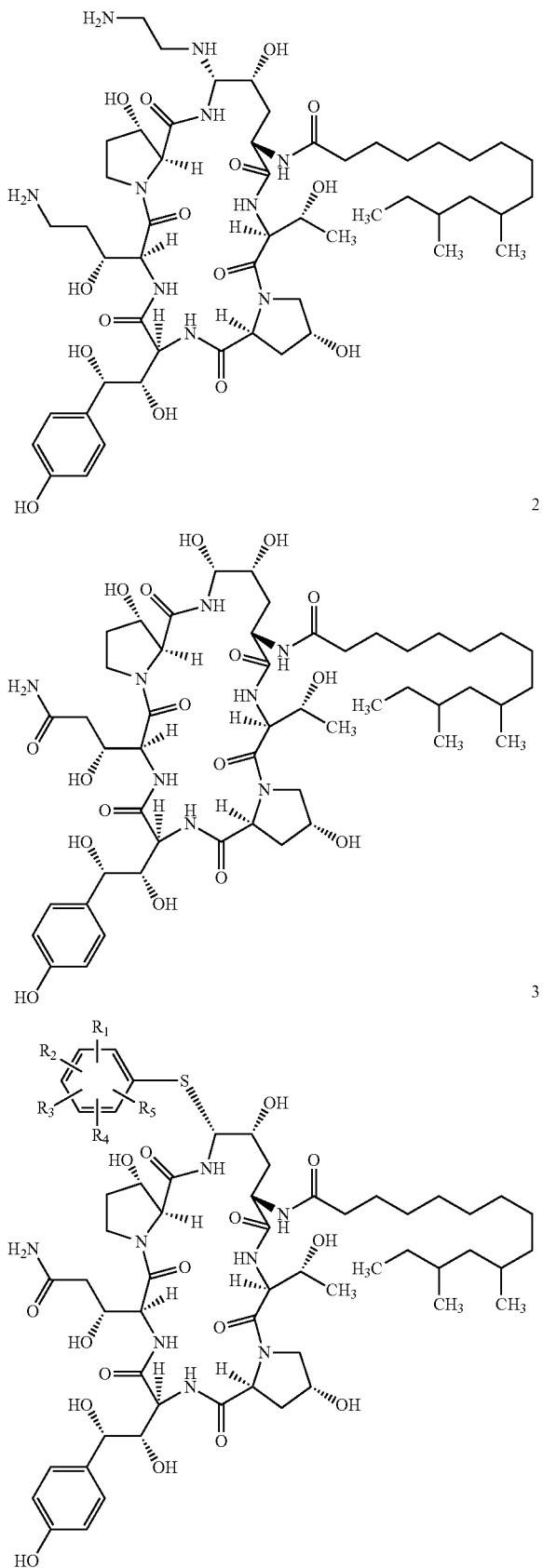

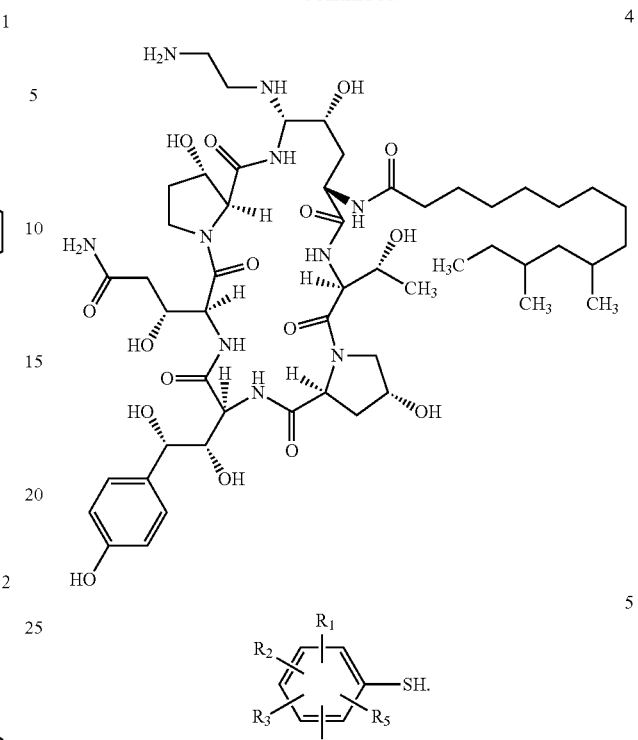

wherein in step (a), the strong leaving-group compound 5 is a sulphydryl-substituted aromatic ring compound, and wherein, in obtaining Formula 3, in the sulphydryl-substituted aromatic ring compound $R_1$ is selected from hydroxy, benzyloxy, phenoxy, substituted phenoxy, or substituted benzyloxy, and $R_2$, $R_3$, $R_4$ and $R_5$ are selected from hydrogen, C1-C6 alkyl, C1-C6 alkoxy, hydroxyl, benzyloxyphenyl, substituted benzyloxyphenyl, nitro, fluorine, chlorine, bromine, or iodine.

2. The preparation method according to claim 1, wherein in the sulphydryl-substituted aromatic ring compound, $R_1$ is selected from hydroxy, benzyloxy, phenoxy, or substituted phenoxy; and $R_2$, $R_3$, $R_4$, and $R_5$ are selected from hydrogen, C1-C4 alkyl, C1-C4 alkoxy, hydroxyl, bromine or nitro.

3. The preparation method according to claim 2, wherein in the sulphydryl-substituted aromatic ring compound, $R_1$ is selected from hydroxy; and $R_2$, $R_3$, $R_4$, and $R_5$ are selected from hydrogen, methyl, or hydroxyl.

4. The preparation method according to claim 3, wherein the sulphydryl-substituted aromatic ring compound is selected from 4-hydroxy thiophenol, 3-hydroxy thiophenol, or 4-hydroxy-3-methyl thiophenol.

5. The preparation method according to claim 4, wherein the sulphydryl-substituted aromatic ring compound is 4-hydroxy thiophenol.

6. The preparation method according to claim 1, wherein in step (a), the compound of Formula 2 is mixed with a strong leaving-group compound dissolved in an acid, wherein said acid is selected from trifluoroacetic acid, triflic acid, camphor sulfonic acid, methanesulfonic acid or p-toluene sulphonic acid.

7. The preparation method according to claim 1, wherein in step (a), the temperature for mixing is −50° C. to 40° C.

8. The preparation method according to claim 1, wherein in step (b), the compound of Formula 3 is mixed with ethylenediamine dissolved in a solvent selected from the following group: methanol, ethanol, tetrahydrofuran, 2-methyl tetrahydrofuran, isopropanol, trifluoroethanol, acetonitrile or dichloromethane.

9. The preparation method according to claim 1, wherein in step (b), the temperature for mixing is 0° C. to 40° C.

10. The preparation method according to claim 1, wherein in step (c), the hydroxyl protectant is selected from boric acid protectants or silicane agents.

11. The preparation method according to claim 1, wherein in step (c), the borane complex is selected from: a complex of borane and tetrahydrofuran, borane and dimethyl sulfide, borane and diphenyl sulfide, borane and dibenzyl sulfide, borane and dioxane, borane and 1,4-oxathiane, or a complex of $BH_2Cl$ and dimethyl sulfide.

12. The preparation method according to claim 1, wherein in step (c), the temperature for mixing is −20° C. to 20° C.

13. The preparation method according to claim 1, wherein in step (a), the temperature for mixing is −20° C. to −15° C.

14. The preparation method according to claim 1, wherein in step (b), the temperature for mixing is 25° C. to 35° C.

15. The preparation method according to claim 1, wherein in step (c), the borane complex is selected from a complex of borane and tetrahydrofuran, or borane and dimethyl sulfide.

16. The preparation method according to claim 1, wherein in step (c), the temperature for mixing is 0° C. to 10° C.

* * * * *